United States Patent
Santiago et al.

(10) Patent No.: US 8,065,928 B2
(45) Date of Patent: Nov. 29, 2011

(54) VENTED FILTER FOR AUTOMATIC HPLC LOOP LOADING

(75) Inventors: Johanna Santiago, Knoxville, TN (US); Thomas Lee Collier, Perkasie, PA (US); Steven Zigler, Knoxville, TN (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 610 days.

(21) Appl. No.: 12/263,620

(22) Filed: Nov. 3, 2008

(65) Prior Publication Data

US 2009/0139310 A1    Jun. 4, 2009

Related U.S. Application Data

(60) Provisional application No. 61/003,002, filed on Nov. 14, 2007.

(51) Int. Cl.
*G01N 30/20* (2006.01)
(52) U.S. Cl. .................................................. 73/863.72
(58) Field of Classification Search .................. None
See application file for complete search history.

(56) References Cited

U.S. PATENT DOCUMENTS

| 5,091,092 A * | 2/1992 | Newhouse et al. ........... 210/635 |
| 2005/0199077 A1* | 9/2005 | Prybella et al. ............ 73/863.86 |

* cited by examiner

*Primary Examiner* — Robert R Raevis
(74) *Attorney, Agent, or Firm* — Peter Kendall

(57) ABSTRACT

A vented filter is placed at the HPLC (High Performance Liquid Chromatography) loop entry port of an HPLC injector valve. The vented filter prevents the push gas used to deliver the crude radiolabeled product from over-pushing the liquid to waste. Push gas is vented off when the entire crude liquid product has passed through the vented filter and been loaded onto the HPLC loop.

13 Claims, 2 Drawing Sheets

VENTED FILTER FOR AUTOMATIC HPLC LOOP LOADING

CROSS-REFERENCE TO RELATED APPLICATIONS

This application claims benefit of co-pending Provisional Application Ser. No. 61/003,002 filed Nov. 14, 2007, pursuant to 35 U.S.C. §119(e).

TECHNICAL FIELD

The present invention is in the field of automated radiochemistry. More specifically, the invention relates to automated HPLC (High Performance Liquid Chromatography) purification of radiotracers or radiolabeled pharmaceuticals.

BACKGROUND OF THE INVENTION

Chromatography is used to separate mixtures of substances into their individual components. The basic principles of chromatography involve a stationary phase (usually a solid or a liquid supported on a solid) and a mobile phase (usually a liquid or a gas). The mobile phase flows through the stationary phase and carries the components of the mixture with it. Since different components travel at different rates, the components separate from each other during the process and can be isolated.

In column chromatography, stationary phase particles are packed into a column and the mobile phase is allowed to flow through the stationary phase. This method relies on gravity to force the mobile phase through the stationary phase. During column chromatography, the smaller the stationary phase particle size, the greater the separation of components. However, smaller particles have greater resistance to flow.

HPLC is an improved form of column chromatography. Instead of a solvent being allowed to drip through a column under gravity, it is forced through the column under high pressures of up to 400 atmospheres, thereby increasing the speed of the process and allowing the use of smaller stationary phase particles. Thus, HPLC allows for improved separation of the components of the mixture.

FIG. 1 is a schematic of a conventional HPLC system 100. A sample mixture 120 is introduced to system 100 through injector valve 130. Injector valve 130 allows sample 120 to be introduced into HPLC loop 140 with any excess sample 120 directed to waste 110. Once sample 120 is in HPLC loop 140, injector valve 130 is activated to allow mobile phase 160 to be pumped into system 100 via pump 150. Pump 150 forces mobile phase 160 through injector valve 130 and HPLC loop 140 and into column 170. Column 170 is filled with a stationary phase 175. As mobile phase 160 is forced through injector valve 130, HPLC loop 140, and column 170, the individual components of sample 120 are separated out. As the separated components flow out of the column, detector 180 analyzes the results.

One common method of detecting substances that have passed through the column uses ultra-violet absorption. Many organic compounds absorb UV light of various wavelengths. Therefore a beam of UV light is directed through the stream of liquid coming out of the column and detected on the opposite side of the stream. The amount of light absorbed will depend on the amount of a particular compound that is passing through the beam at the time. Based on the output of the detector, it is possible to identify the separated components of the sample.

Conventional HPLC is often employed as a method of analysis of different components in a given sample. In the production of radiolabeled pharmaceuticals, the radiolabeled pharmaceutical synthesis step is often followed by a purification step. HPLC is one purification method to isolate the radiolabeled pharmaceutical from the synthesis mixture. In a radiolabeled pharmaceutical HPLC purification system, a radiation detector is used along with the UV detector to identify the components of the sample. The detection of a peak in the UV or radiation detector signal indicates the presence of the radiolabeled pharmaceutical. A valve following the detectors is installed to direct fluid flow to either a waste vial or to a product collection vial. Once the UV chromatogram peak or the radiation chromatogram peak of the desired radiolabeled pharmaceutical appears, the valve is switched to collect this product.

As mentioned above, the first step of the HPLC process is to load a specific amount of the sample to be purified/separated into a fixed volume HPLC loop. The other end of the loop is directed to waste to catch any waste that overflows from the loop. In a regular HPLC setup, the sample is injected into the loop with a syringe and overflows to waste are common. However, in the production of radiolabeled pharmaceuticals, it is desirable to avoid overflows to waste, thereby minimizing process loss. Further complicating the process is that the task of loading the loop is often automated.

One efficient way of transporting liquid is by using a push gas to push liquid through a series of tubes. The push gas has to be turned off at the right time to avoid sending the crude radiolabeled product to waste. Prior systems use a bubble detector or a liquid detector to determine when the radiolabeled product has been completely loaded into the HPLC loop and to stop the push gas. However, these systems are unreliable.

Therefore, it is desirable to have a reliable device to automatically limit the amount of sample that is injected into the HPLC loop.

SUMMARY OF THE INVENTION

With a vented filter at the HPLC loop entry port of an HPLC injector valve, the push gas used to deliver the crude radiolabeled product will not over push the liquid to waste. Push gas is vented off when the entire crude liquid product has passed through the vented filter and been loaded onto the HPLC loop.

BRIEF DESCRIPTION OF THE DRAWINGS

The invention will now be described in greater detail in the following by way of example only and with reference to the attached drawings, in which.

DETAILED DESCRIPTION OF THE INVENTION

Figure 1:
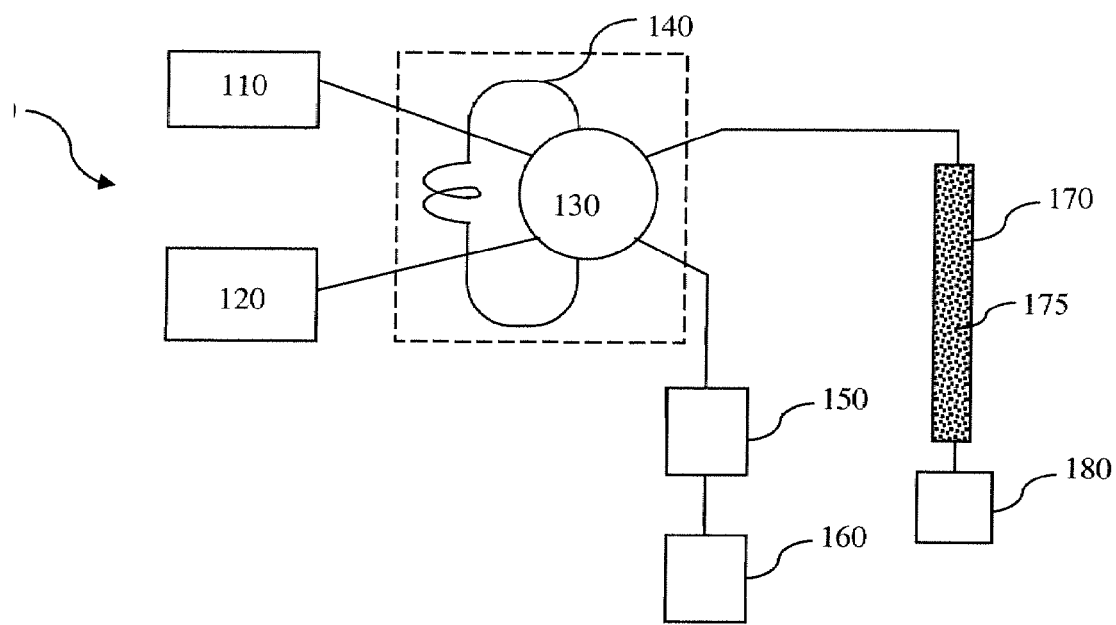
FIG. 1 is a schematic of a conventional HPLC system.

As required, disclosures herein provide detailed embodiments of the present invention; however, the disclosed embodiments are merely exemplary of the invention that may be embodied in various and alternative forms. Therefore, there is no intent that specific structural and functional details should be limiting, but rather the intention is that they provide a basis for the claims and as a representative basis for teaching one skilled in the art to variously employ the present invention.

As mentioned above, FIG. 1 discloses a conventional High Performance Liquid Chromatography (HPLC) system 100. A mixture sample 120 is introduced to system 100 through injector valve 130. Sample 120 may be a radiolabeled product such as a radiolabeled pharmaceutical. Injector valve 130 allows sample 120 into HPLC loop 140 with any excess sample 120 directed to waste 110.

Once sample 120 is in HPLC loop 140, injector valve 130 is switched to allow mobile phase 160 to be pumped through the HPLC loop via pump 150. Mobile phase 160 may be any suitable eluent. Furthermore, mobile phase 160 may consist of a plurality of eluents used successively to help promote greater separation of the components of the sample.

Pump 150 forces mobile phase 160 through injector valve 130 and HPLC loop 140 and into column 170. Pump 150 may be able to force mobile phase 160 through at pressures upwards of 400 atmospheres. Column 170 is filled with a stationary phase 175. Stationary phase 175 may consist of particles with a diameter of less than ten microns. As mobile phase 160 is forced through injector valve 130, HPLC loop 140, and column 170, the components of sample 120 are chromatographically separated out. Once the separation is complete, detector 180 analyzes the results. Detector 180 may be an ultraviolet absorption detector and/or a radiation detector. Once the UV chromatogram peak or the radiation chromatogram peak of the desired radiolabeled pharmaceutical appears, a valve located downstream from the detectors is switched to collect the product. After the chromatogram peak of the desired product has passed, the valve is switched back to waste.

Figure 2A:
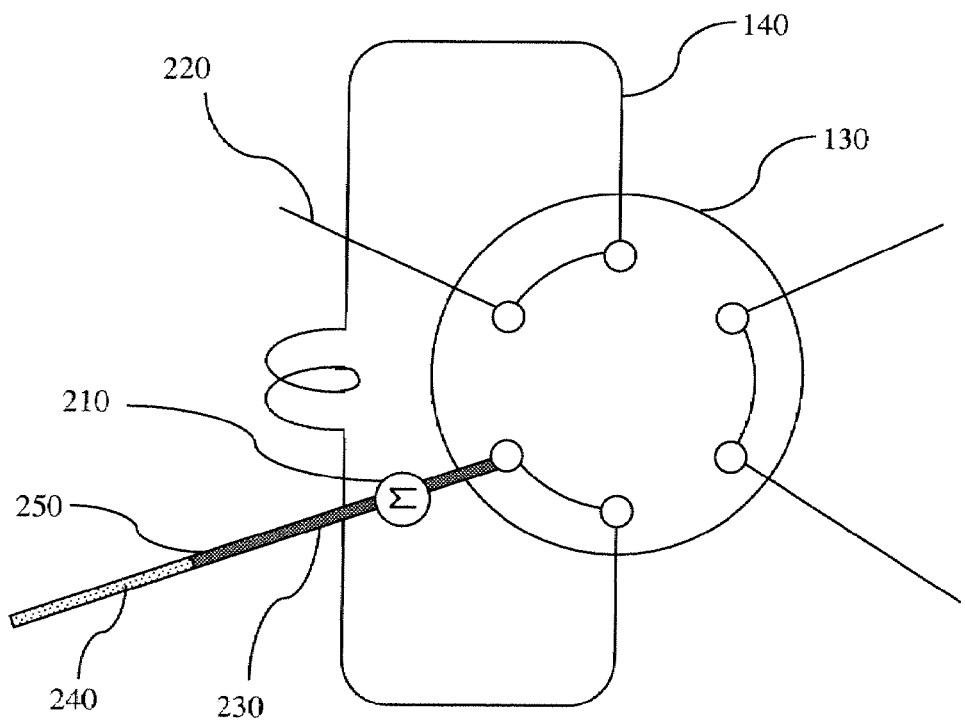
FIGS. 2(a)-2(b) show a system in accordance with the invention before and after the gas has been vented off, respectfully.
Figure 2B:
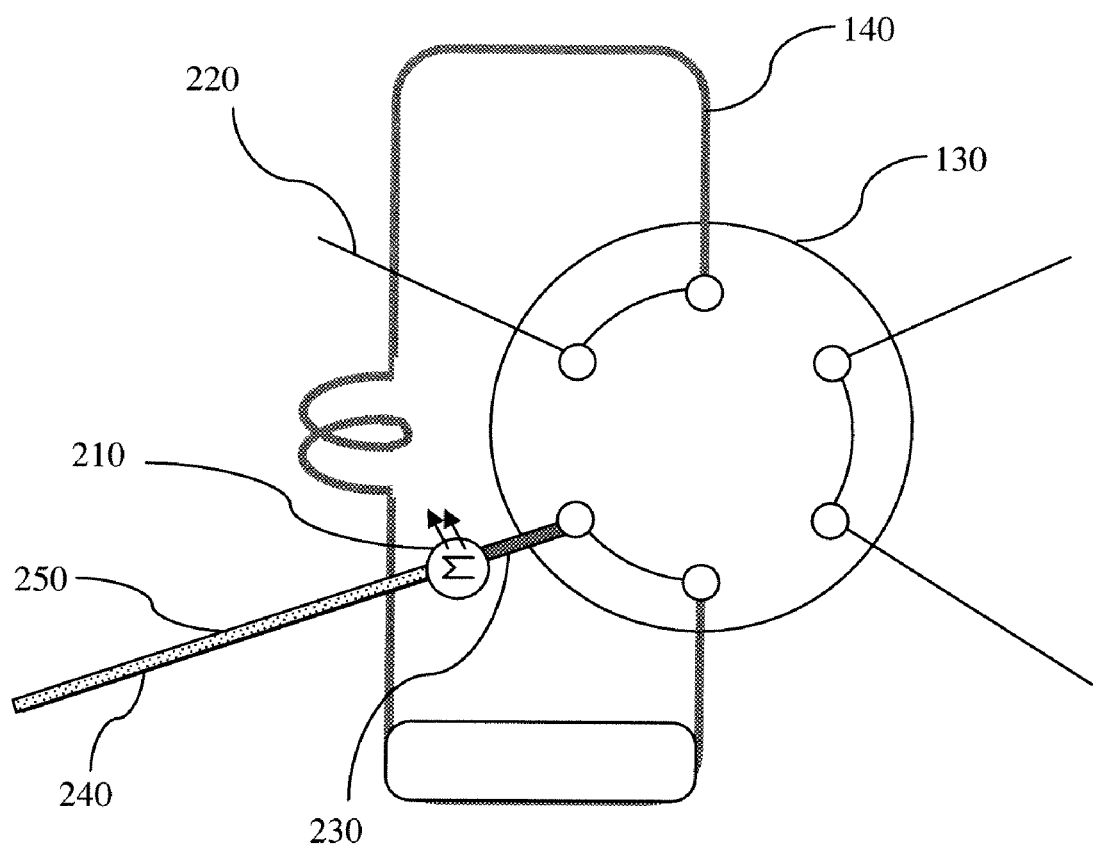

FIGS. 2(a) and 2(b) are close-up views of the area within the dashed box in FIG. 1, modified in accordance with the present invention. FIG. 2(a) depicts the present invention in the state of injecting the sample 230 through injector valve 130 into HPLC loop 140. Sample 230 is pushed through sample feed tube 250 by a gas 240. The sample passes through vented filter 210 as it enters injector valve 130.

FIG. 2(b) depicts the system of the present invention once the gas 240 has reached vented filter 210. i.e., after all of the liquid sample 230 has passed through the vented filter 210 and loaded onto the HPLC loop. To prevent the gas 240 from pushing sample 230 into waste tube 220, the gas 240 is vented off by vented filter 210, thereby precluding gas 240 from entering into the HPLC loop.

Vented filter 210 may be located such that a set amount of sample 230 is allowed to enter HPLC loop 140 before the gas 240 is vented off. Vented filter 210 may be any device capable of venting of gas from a feed tube.

While the invention has been disclosed with reference to specific exemplary embodiments, modifications to and departures from the disclosed embodiments will occur to those having skill in the art. Accordingly, what is protected is defined by the scope of the following claims.

What is claimed is:

1. A high performance liquid chromatography (HPLC) device, comprising:
an injector valve;
a sample feed for injecting a sample into said injector valve, wherein the sample feed uses gas to inject the sample into the injector valve;
a vented filter located between the sample feed and the injector valve, to vent off the gas from the sample feed after said sample has passed through the vented filter; and
a loop for receiving the sample from the injector valve.

2. The HPLC device of claim 1, further comprising:
at least one mobile phase material for carrying the sample;
a pump for forcing the at least one mobile phase material through the injector valve and the loop;
a column filled with stationary phase material for receiving the sample carried by the at least one mobile phase material; and
a detector for analyzing the sample as it passes through the column.

3. The HPLC device of claim 2, wherein the stationary phase material has a particle size of less than 10 microns.

4. The HPLC device of claim 2, wherein the pump forces the at least one mobile phase material through the injector at less than 400 atmospheres of pressure.

5. The HPLC device of claim 2, wherein the detector is an ultra-violet absorption detector and/or a radiation detector.

6. The HPLC device of claim 1, wherein the sample is a radiolabeled product.

7. The HPLC device of claim 1, further comprising a waste receptacle coupled to said injector valve.

8. A method of analyzing a sample and isolating a desired component within said sample using high performance liquid chromatography (HPLC), comprising the steps of:
forcing a sample through an injector valve into a loop via a feed tube using a push gas;
venting off the gas from the feed tube once a set amount of the sample has entered the loop;
forcing a mobile phase material and the sample through the loop and into a column filled with stationary phase material;
further forcing the mobile phase material and the sample through the stationary phase material in the column, thereby separating the sample into its components;
analyzing the results of the separation as it exits the column;
outputting the analyzed results; and
isolating the desired component based on the chromatogram as the chromatogram is being generated.

9. The method of claim 8, wherein the outputted analyzed results are on at least one of a computer monitor, a printout, and an electronic readable media.

10. The method of claim 8, wherein the sample is the unpurified form of a radiolabeled product.

11. The method of claim 8, wherein the desired component is a radiolabeled pharmaceutical.

12. The method of claim 8, further comprising using different mobile phase materials successively.

13. The method of claim 8, wherein the sample is analyzed using an ultra-violet absorption detector and/or a radiation detector.

* * * * *